United States Patent [19]

Tritten

[11] 4,179,485
[45] Dec. 18, 1979

[54] BONE PROSTHESIS AND METHOD OF MANUFACTURE THEREOF

[75] Inventor: Paul Tritten, Tarbes, France

[73] Assignee: Ceraver, France

[21] Appl. No.: 869,292

[22] Filed: Jan. 13, 1978

Related U.S. Application Data

[63] Continuation-in-part of Ser. No. 739,789, Nov. 8, 1976, abandoned, which is a continuation of Ser. No. 434,685, Jan. 18, 1974, abandoned.

[30] Foreign Application Priority Data

Jan. 18, 1973 [FR] France .............................. 73 01668

[51] Int. Cl.² .............................................. C04B 35/10
[52] U.S. Cl. ........................................ 264/44; 264/60; 264/63; 264/66; 264/67
[58] Field of Search .................. 264/44, 56, 66, 63, 264/67, 60; 3/1

[56] References Cited

U.S. PATENT DOCUMENTS

| 2,947,056 | 8/1960 | Csordas et al. | 264/56 |
| 3,505,158 | 4/1970 | Murray | 264/60 |
| 3,605,123 | 9/1971 | Hohn | 3/1 |
| 3,713,860 | 1/1973 | Auskein | 3/1 |

FOREIGN PATENT DOCUMENTS 2096985  3/1972 France .............................. 3/1

OTHER PUBLICATIONS

Cahoon, "Sintering and Grain Growth of Alpha Alumina", J. Am. Cir. Soc., vol. 39, #10, pp. 337-344 (1956).
Chatteyie et al., "Effect of Processing Variables on the Properties of High Aluminum Ceramics", Glass and Ceramic Bulletin, vol. 23, #4, 1976.

Primary Examiner—Robert F. White
Assistant Examiner—John A. Parrish
Attorney, Agent, or Firm—Craig and Antonelli

[57] ABSTRACT

Method for manufacturing a bone prosthesis made of porous alumina. Calibrated alumina grains are subjected to firing at a temperature lower than their sintering temperature; they are disintegrated, then compressed into a pressed mass, then the latter is subjected to sintering.

8 Claims, 2 Drawing Figures

BONE PROSTHESIS AND METHOD OF MANUFACTURE THEREOF

This application is a continuation-in-part of application Ser. No. 739,789, filed Nov. 8, 1976, now abandoned, which is a continuation of application Ser. No. 434,685, filed Jan. 18, 1974, now abandoned.

The present invention concerns a method of manufacturing a bone prosthesis comprising at least partly a porous alumina having calibrated pore dimensions greater than 30 microns. It bears more particularly on a method of manufacturing a bone prosthesis comprising a dense first part made of alumina and at least another part made of porous alumina, intended for ensuring the connection of the first part with the natural bone. It is applied more particularly to bone prostheses in joints, such as those which were the object of British Pat. No. 1,334,584 of Oct. 24, 1973, and of U.S. Pat. No. 3,871,031. It is applied also to methods of manufacturing substitutions of a part of a bone comprising or not comprising a joint.

Bone prosthesis must meet three essential requirements: be inert to any action of biological media, have a mechanical strength compatible with the efforts to be transmitted and have a structure in the parts to be connected together to the residual bone such that it promotes bone reconstitution or retention. According to the above British patent, the acetabular part of a prosthesis of the hip may have a convex outside portion made of porous alumina having pore dimensions ranging from 10 to 30 microns, assembled to a non-porous alumina inside portion. That assembling is, however, mechanically delicate to perform and the pores have dimensions which are insufficient to enable a solid connection by rapid rebuilding of the bone. French Pat. No. 2,106,242 describes a bone prosthesis made of porous alumina having pores dimensions between 75 and 150 microns.

The above U.S. Pat. No. 3,871,031 discloses a structure of the inside portion of the part intended to be fixed to the remaining part of the bone, comprising anfractuosities, for example grooves, at least two of whose dimensions are in the order of a millimeter, so as to enable a more rapid and more complete rebuilding of the bone. This requires, however, a relatively complicated machining of a part having great hardness. Moreover, if the alumina is effectively suitable for producing prosthesis elements to be subjected essentially to compression, by reason of its high mechanical resistance to that stress, it is less suitable as a material for prosthesis elements subjected more particularly to bending.

Use is therefore made of a production based on metals inert to biological media, such as titanium or metal alloys, more particularly stainless nickel-cobalt-chromium steel, cobalt-chromium alloy or, even, titanium alloys. It would be possible to provide for depositing, on the portion of the metallic part of the prosthesis which is to be connected to the bone, a layer of alumina having sufficient porosity to enable rapid rebuilding of the bone, for example by projection with a plasma torch. That depositing is difficult to effect; the solidity of its connection to the metallic portion is questionable and keeping the optimum porosity is hazardous. It is therefore still a practice, in general, to make use of organic cements, for example acrylic resins, although the tolerance of the biological medium to such cements and the resistance of such cements throughout time still give rise to certain misgivings.

An object of the invention is to obviate the above disadvantages and to manufacturing a bone prosthesis of given porosity and pore size enabling a connection with the natural part of the bone by rebuilding of the bone, that is, by the reconstitution or retention of new bone cells coming from the residual bone and invading pores formed in the newly inserted prosthesis, that connection being formed quickly and having good solidity.

The method for manufacturing a bone prosthesis according to the invention is characterized in that a powder of substantially pure alumina is granulated with an organic binder into grains of a size between about 0.5 and 1.5 millimeters, said grains are fired in bulk to a temperature of at least 1.400° C. but lower than their sintering temperature, then are disintegrated, then compressed at a pressure of at least one metric ton/cm$^2$ into a first pressed mass, and finally are sintered at a temperature of about 1.650°–1.700° C. to form said porous alumina.

It comprises, moreover, preferably at least one of the following characteristics:

The granulation of the powder of substantially pure alumina is carried out by roto-granulation.

The firing of the grains of alumina is effected at a temperature of about 1.400° C.

The sintering is carried out in an oxidizing atmosphere.

The sintering is effected at a temperature of about 1.650° C. for at least about 4 hours.

The compressing of the grains of alumina after the firing thereof is effected at a pressure of about 1 to 4 metric tons per square cm.

The dimension of the grains of alumina is comprised between 0.5 and 0.8 mm approximately.

Other grains of alumina are compressed into a pressed mass without previous firing, then are subjected to sintering with a pressed mass of previously fired grains, so as to produce a prosthesis comprising a dense alumina portion.

The compressed grains of alumina which have not previously been fired are finer than those which are compressed after having previously been fired.

The pressed mass intended for forming the porous alumina and that intended for forming the dense alumina are pressed in a same mould having a shape corresponding to that of the part to be produced, preferably after previous pressing.

The bone prosthesis obtained by the above defined method is characterized in that the dimension of the pores of the porous alumina is comprised between 100 and 200 microns approximately, and the porosity of the alumina is about 30 %. It comprises, moreover, preferably a metallic portion in which porous alumina parts are fixed either by inclusion, the said alumina then constituting a core arranged in a mould in which the metallic portion is cast, or by crimping, screwing, clamping or a like operation.

The following text describes, by way of an example and with reference to the accompanying drawing, a coxo-femoral prosthesis and a prosthesis of a phalanx of a finger manufactured according to the invention.

Figure 1:
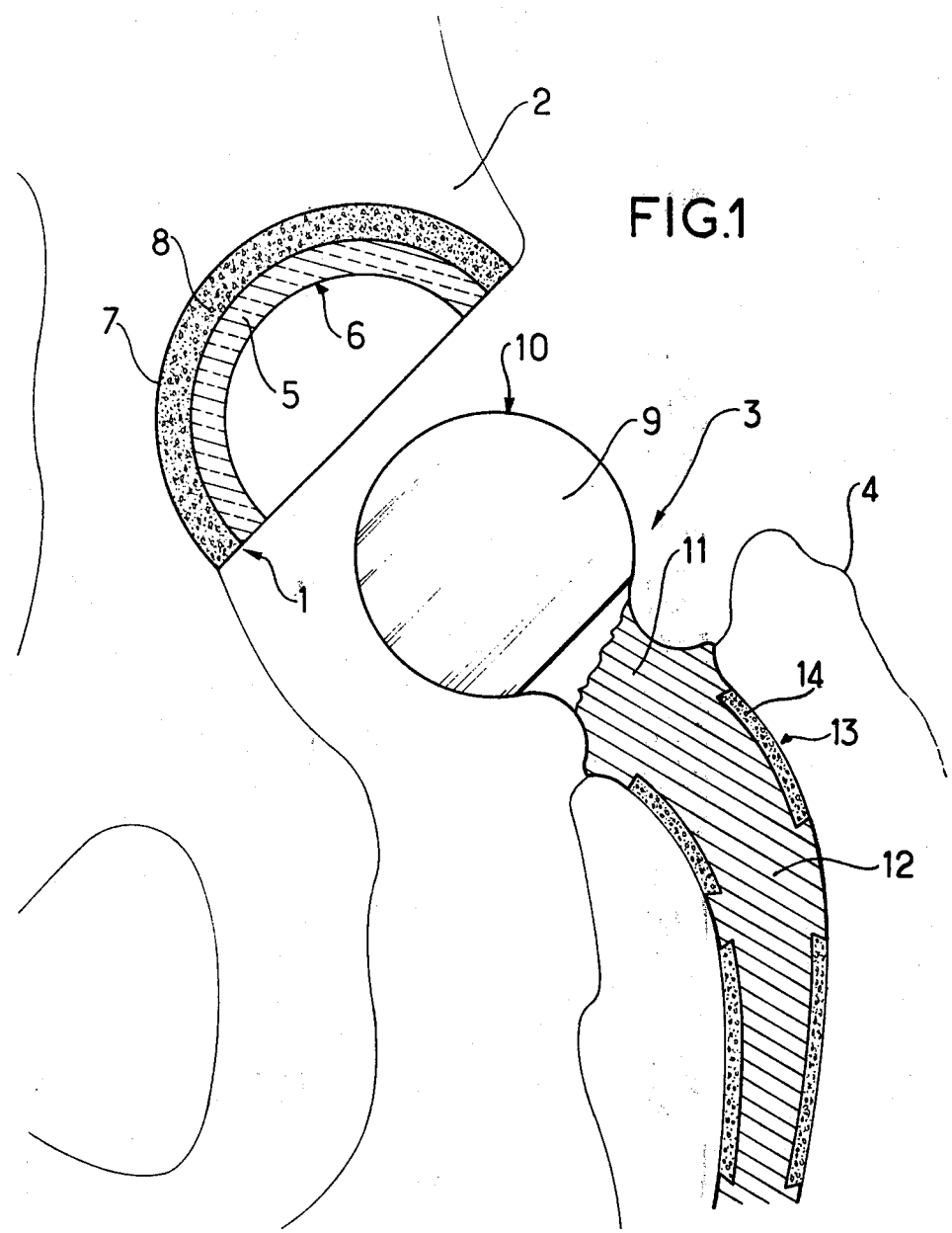
FIG. 1 shows a coxo-femoral prosthesis having mating surfaces made of polished compact sintered alumina.

In FIG. 1, the coxo-femoral prosthesis comprises an acetabular part 1 fixed to the cotyle of the hip 2 and a femoral part 3 fixed to the thigh bone 4, the two parts being shown spaced apart from each other for clearness' sake. The acetabular part comprises an inside part 5 made of compact sintered alumina, whose concave spherical surface 6 is polished. Its outside part 7, coming into contact with the bone of the cotyle, has a porosity of about 30 % and its pores 8 have a dimension comprised between about 100 and 200 microns, enabling the penetration of the bone cells for rebuilding of the bone, in order to ensure its solid fixing in the cotyle.

The femoral part 3 consists of a spherical head 9 made of compacted sintered alumina, having a polished convex surface 10, intended to be fitted in the concave surface 6 of the acetabular part, so as to form an anti-friction joint. That head is connected through a neck 11 to a rod 12 embedded in the femur, the neck and the rod being made of a biologically acceptable metal or metallic alloy, such as a nickel-cobalt-chromium alloy, a titanium alloy; the neck is fixed to the head 9 through a stud (not shown) inserted in a cylindrical cavity of the head and cemented to the latter by means of a cement tolerated by the human tissues, for example as described in the above-mentioned British Pat. No. 1,334,584.

The rod 12 is formed by casting a metal in a mould containing cores 13 made of sintered alumina having a porosity of about 30 %, whose pores 14 have dimensions comprised between 100 and 200 microns. These cores generally have the shape of a dovetail, so as to ensure a solid mechanical connection between these cores and the rod itself.

The porous alumina portion of the femoral part is obtained by the following operations:

One granulates first an alumina powder by rotation in an inclined rotating tank with controlled projection through a gun of an agglomerating binder, such as the polyvinyl alcohol of the trade name Rhodoviol BS 125 of Rhone-Poulenc, in a 5-10% aqueous solution, plasticized with 5% of glycerol (in relation to the amount of polyvinyl alcohol). One can also use as binder a 50% emulsion of polyvinyl acetate, such as that of the trade name Rhodopas of Rhone-Poulenc, already plasticized and diluted according to the needs of the pulverization, or a solution of an acrylic resin in a volatile organic solvent. The grains are screened at the outlet to keep those of a diameter between 0.5 and 0.8 mm: the fines are returned to the rotating tank, the too large grains are discarded. The mean dimension of the grains is adjusted by the feed rate of the powder and the slope of the tank. The grains have a density of about 2 and a spherical shape.

One can also prepare the grains by spraying a fine alumina slip and screening the grains, but the yield in granules of the appropriate dimension is lower.

The grains are then fired in bulk to about 1.400° C. in an oxidizing atmosphere in a gas oven during about 4 hours. After the firing, the granules have a density of about 3.7.

The fired grains are then midly disintegrated and mixed with an appropriate binder, such as the available under the trade name Carbowax or glycol stearate. For instance, they are agglomerated under a pressure of 1 to 4 metric tons/square cm in a mould with the binder. Because of the cohesion imparted thereto by the firing, the grains withstand the pressure of agglomeration and keep their spherical shape. Then, after firing at 300° C. for eliminating the binder, they are sintered in an oxidizing atmosphere at about 1.650° C. during 4 hours.

By that method, it is possible to obtain parts having various shapes: strip plates, bars, tubes, having a porosity of 30%, with pore dimensions comprised between 100 and 200 microns, whose mechanical tensile strength is in the order of 250 to 300 kg per square cm. These parts are then used as foundry cores arranged in moulds provided for the casting of the femoral rod, in such a way that these cores be solidly fixed therein, constituting, however, a portion of the surface of the femoral part, that portion giving rise to bone rebuilding ensuring the solid fixing of the femoral rod in the thigh bone.

Inasmuch as concerns the acetabular part, which is partly made of non-porous alumina, the porous portion provided for the rebuilding of bone may be formed at the same time as the non-porous portion, the two portions then being connected together by the ceramic production method used.

In that case:

In a first operation, as has been described previously, a pressed mass is prepared, based on previously fired grains;

In a second operation, also in a like manner, a pressed mass is prepared, based on finer grains obtained by spray drying a paste containing approximately 8% of binding agent basically containing carboxymethyl or carboxyethylcellulose, for example the binding agent sold under the trade name Carbowax, these grains not being previously fired. The final operation for putting into shape the compound part (porous alumina, non-porous alumina) is effected by filling the mould with one mass and the other, possibly pre-pressed separately. After pressing together at a pressure comprised between 1 and 4 metric tons per square cm, the raw part obtained is fired at 300° C., then subjected to sintering at 1.650° C. in an oxidizing atmosphere during 4 hours. The portion constituted by the usual pressed mass is non-porous; the portion constituted by grains previously fired has the above-mentioned porosity of 30%. The two portions are perfectly connected together.

Figure 2:
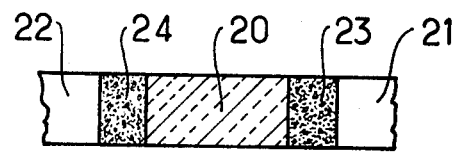
FIG. 2 shows a prosthesis of a phalanx of a finger.

In FIG. 2, the prosthesis of a phalanx of a finger comprises a cylinder 20 made of dense sintered alumina arranged between two portions of residual bone 21 and 22. The cylinder leads at each end to the parts 23, 24, made of sintered alumina having a porosity close to 30%, with pore dimensions ranging from approximately 100 to 200 microns.

The prosthesis as a whole is manufactured in a way similar to that described hereinabove with respect to the acetabular part in FIG. 1.

The invention may be applied to other prostheses than that of the hip or of a phalanx of a finger, for example, to the prosthesis of the shoulder or of another joint, or to that of any other bone of the skeleton.

While I have shown and described several embodiments in accordance with the present invention, it is understood that the same is not limited thereto, but is susceptible of numerous changes and modifications as known to a person skilled in the art, and I therefore do not wish to be limited to the details shown and described herein but intend to cover all such changes and modifications as are obvious to one of ordinary skill in the art.

What is claimed is:

1. A method for manufacturing a bone prosthesis formed at least in part from substantially pure porous alumina and having porosity of about 30% and a pore size of about 100 to 200 microns, comprising granulating a powder of substantially pure alumina with an organic binder into grains of a size between about 0.5 and 1.5 millimeters, heating said grains in bulk to a temperature of at least 1.400° C., but lower than their sintering temperature, disintegrating the bulk so heated, compressing the disintegrated alumina grains at a pressure of at least about 1 metric ton per square centimeter into a first pressed mass, and sintering said first pressed mass at a temperature of about 1.650°–1.700° C. to form said porous alumina.

2. A method according to claim 1, wherein the granulation of the powder of substantially pure alumina is carried out by roto-granulation.

3. A method according to claim 1, wherein said first pressed mass is sintered in an oxidizing atmosphere.

4. A method according to claim 3, wherein said first pressed mass is sintered at a temperature of about 1.650° C. for at least about 4 hours.

5. A method according to claim 4, wherein the pure alumina powder is granulated into grains of a size between 0.5 and 0.8 millimeters.

6. A method according to claim 1, further comprising compressing fine alumina grains with an organic binder into a second pressed mass without previous firing and disintegrating, said fine ceramic grains having a grain size substantially finer than that of the alumina grains subjected to firing and disintegrating, and then sintering said first pressed mass and said second pressed mass together so as to produce a prosthesis comprising a porous alumina portion and a dense alumina portion.

7. A method according to claim 2, further comprising compressing fine alumina grains with an organic binder into a second pressed mass without effecting any previous firing or disintegrating thereof, said fine alumina grains having a grain size substantially finer than the alumina grains subjected to firing and disintegrating prior to the formation of the first pressed mass and then sintering said first pressed mass and said second pressed mass together so as to produce a prosthesis comprising a porous alumina portion from said first pressed mass and a dense alumina portion from said second pressed mass.

8. A method according to claim 1 wherein the bulk is disintegrated to provide a plurality of separate disintegrated alumina grains, the separate disintegrated alumina grains are admixed with an organic binder, then the resulting admixture is compressed within a mold to form said first pressed mass and the pressed mass is then fired to remove the organic binder prior to being sintered at about 1,650°–1700° C. to form the bone prosthesis made of said porous alumina.

* * * * *